United States Patent

Murdock

[11] Patent Number: 6,004,577
[45] Date of Patent: Dec. 21, 1999

[54] ENHANCED ELECTROTRANSPORT OF THERAPEUTIC AGENTS HAVING POLYBASIC ANIONIC COUNTER IONS

[76] Inventor: Thomas O. Murdock, 3999 Clover Ave., Vadnais Heights, Minn. 55127

[21] Appl. No.: 08/909,678

[22] Filed: Aug. 12, 1997

[51] Int. Cl.⁶ .................................................. A61K 9/70
[52] U.S. Cl. ........................ 424/443; 424/400; 424/448; 424/449; 514/788; 514/772; 514/318
[58] Field of Search ...................................... 424/400, 443, 424/448, 449; 514/772, 788, 318; 604/20; 128/172.1

[56] References Cited

U.S. PATENT DOCUMENTS

| | | | |
|---|---|---|---|
| 3,991,755 | 11/1976 | Vernon et al. | 128/172.1 |
| 4,141,359 | 2/1979 | Jacobsen et at. | 128/172.1 |
| 4,250,878 | 2/1981 | Jacobsen et al. | 128/207.21 |
| 4,383,529 | 5/1983 | Webster | 604/20 |
| 4,398,545 | 8/1983 | Wilson | 128/798 |
| 4,474,570 | 10/1984 | Ariura et al. | 604/20 |
| 4,722,726 | 2/1988 | Sanderson et al. | 604/20 |
| 4,731,049 | 3/1988 | Parsi | 604/20 |
| 4,767,401 | 8/1988 | Seiderman | 604/20 |
| 4,871,352 | 10/1989 | Tran | 604/82 |
| 4,886,489 | 12/1989 | Jacobsen et al. | 604/20 |
| 4,927,408 | 5/1990 | Weinshenker et al. | 604/20 |
| 5,068,226 | 11/1991 | Weinshenker et al. | 514/58 |
| 5,080,646 | 1/1992 | Theeuwes et al. | 604/20 |
| 5,085,749 | 2/1992 | Grimshaw et al. | 204/182.1 |
| 5,147,296 | 9/1992 | Theeuwes et al. | 604/20 |
| 5,169,382 | 12/1992 | Theeuwes et al. | 604/20 |
| 5,169,383 | 12/1992 | Gyory et al. | 604/20 |
| 5,298,017 | 3/1994 | Theeuwes et al. | 604/20 |
| 5,443,442 | 8/1995 | Phipps et al. | 604/20 |

FOREIGN PATENT DOCUMENTS

| | | |
|---|---|---|
| 0 449 463 A2 | 10/1991 | European Pat. Off. ..... A61K 31/415 |
| 410009 | 10/1933 | Germany . |
| WO96/02232 A1 | 2/1996 | WIPO .............................. A61K 9/00 |

OTHER PUBLICATIONS

Thysman, et al., Anesth Anbalg. 1993; 77:61–66, "In Vivo Iontophoresis of Fentanyl and Sufentanil in Rats: Pharmacokinetics and Acute Antiociceptive Effects.".

Lux, H.D., Neuropharmacology. 1974. 13. pp. 509–517, "Fast Recording Ion Specific Microelectrodes: Their Use in Pharmacological Studies in the CNS.".

Orlov, et al., Moscow VESTNIK AKADEMI MEDITSINSKIKH NAUK SSSR in Russian No. 7, 1974, pp.27–31, "Specificity of Neurochemical Mechanisms of processing Nociceptive Stimulation of Neurons of Difference Structures of the Rabbit Brain." (English and Russian Version).

*Primary Examiner*—Jose' G. Dees
*Assistant Examiner*—Kathryne E. Shelborne

[57] ABSTRACT

Improved electrotransport of therapeutic agents which include agent cations and polybasic anionic counterions. Improved electrotransport is obtained by treating the therapeutic agent with a multivalent metal compound of the formula MX where M is a metallic cation having a valency of at least +2 and is reactive with the polybasic anionic counter ion and X is a pH-increasing anion. Reduction in species which compete with the therapeutic agent for electrotranport is obtained.

30 Claims, 1 Drawing Sheet

ENHANCED ELECTROTRANSPORT OF THERAPEUTIC AGENTS HAVING POLYBASIC ANIONIC COUNTER IONS

TECHNICAL FIELD

The invention relates generally to improved electrotransport drug delivery methods. More specifically, this invention relates to methods for improving the flux of therapeutic agents having polybasic anionic counter ions which are iontophoretically delivered.

BACKGROUND OF THE INVENTION

Transdermal delivery of drugs or therapeutic agents is an important medicament administration route. Transdermal drug delivery bypasses gastrointestinal degradation and hepatic metabolism, while at the same time providing slow, but controlled, systemic delivery of a drug or an agent to a patient's blood stream. It is an especially attractive administration route for drugs or agents with a narrow therapeutic index, short half-life and potent activity.

Transdermal permeation of most compounds is a passive diffusion process. The maximum flux of agent through a patient's skin, i.e., the quantity of agent delivered through a given area of skin, is primarily determined by the drug's partition coefficient and solubility characteristics. Transdermal permeation, however, can be enhanced by iontophoresis.

Iontophoresis is a process by which the transdermal transport of therapeutic agents or drug is increased or controlled using electro-repulsion as the driving force. By the application of an external electrical field to, e.g., an agent-containing reservoir of an electrotransport device, drugs or agents of like charge are driven by repulsive forces through the skin. As such, the transdermal delivery becomes a more controllable, rather than a passive, process, and agent or drug transport flux is thereby increased.

Iontophoretic devices have been known since the early 1900's. A 1934 British Patent Specification No. 410,009 describes a portable iontophoretic device which overcame one of the disadvantages of earlier devices, namely that the patient needed to be immobilized near the current source. More recently, a number of United States patents have issued in the iontophoresis field, indicating a renewed interest in this mode of drug delivery. For example, Vernon et al., U.S. Pat. No. 3,991,755; Jacobsen et al., U.S. Pat. No. 4,141,359; Wilson, U.S. Pat. No. 4,398,545; and Jacobsen, U.S. Pat. No. 4,250,878, disclose examples of iontophoretic devices and some applications thereof.

In presently known iontophoresis devices, at least two electrodes are used. Both of these electrodes are disposed so as to be in intimate electrical contact with some portion of the skin of the body. One electrode, called the "active" or donor electrode, is the electrode from which the ionic (or ionizable) agent, drug precursor or drug is delivered into the body via the skin by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery.

Depending upon the electrical charge of the species to be delivered transdermally, either the anode or cathode may be the "active" or donor electrode. If, for example, the ionic substance to be driven into the body is positively charged, then the anode will be the active electrode and the cathode will serve to complete the circuit. On the other hand, if the ionic substance to be delivered is relatively negatively charged, then the cathodic electrode will be the active electrode and the anodic electrode will be the counter electrode.

Alternatively, both the anode and the cathode may be used to deliver drugs of appropriate charge into the body. In such a case, both electrodes are considered to be active or donor electrodes. For example, the anodic electrode can drive positively charged substances into the body while the cathodic electrode can drive negatively charged substances into the body.

Existing iontophoresis devices generally require a reservoir or source of the ionized or ionizable species (or a precursor of such species) which is to be iontophoretically delivered or introduced into the body. Examples of such reservoirs or sources of ionized or ionizable species include a pouch as described in the previously mentioned Jacobsen, U.S. Pat. No. 4,250,878, a pre-formed gel body as disclosed in Webster, U.S. Pat. No. 4,382,529, and a generally conical or domed molding of Sanderson et al., U.S. Pat. No. 4,722,726. Such drug reservoirs are electrically connected to the anode or to the cathode of an iontophoresis device to provide a fixed or renewable source of one or more desired species or agents.

More recently, iontophoretic delivery devices have been developed in which the donor and counter electrode assemblies have a "multi-laminate" construction. In these devices, the donor and counter electrode assemblies are each formed by multiple layers of (usually) polymeric matrices. For example, Parsi, U.S. Pat. No. 4,731,049, discloses a donor electrode assembly having hydrophilic polymer based electrolyte reservoir and drug reservoir layers, a skin-contacting hydrogel layer, and optionally one or more semipermeable membrane layers. In addition, Ariura et al., U.S. Pat. No. 4,474,570, discloses a device wherein the electrode assemblies include a conductive resin film electrode layer, a hydrophilic gel reservoir layer, and aluminum foil conductor layer and an insulating backing layer.

Hydrogels have been particularly favored for use as the drug reservoir matrix and electrolyte reservoir matrix in iontophoretic delivery devices, in part, due to their high equilibrium water content and their ability to quickly absorb water. In addition, hydrogels tend to have good biocompatibility with the skin and with mucosal membranes.

Iontophoresis has been used for both the local and systemic delivery of drugs. The iontophoresis process has been useful in the transdermal administration of any number of medicaments or drugs. The control of electrical factors, such as intensity, profile and duration of electrical current application, as well as physicochemical factors, such as the pH or ionic strength, allows one to modulate the rate and the duration of permeation. As intended herein, the particular therapeutic agent to be delivered may be completely charged (i.e., 100% ionized), completely uncharged, or partly charged and partly uncharged. The therapeutic agent or species may be delivered by electromigration, electroosmosis or a combination of the two. Electroosmosis, in general, results from the migration of solvent, in which the species is contained, as a result of the application of electromotive force to the therapeutic species reservoir.

Of particular interest is the transdermal delivery of analgesic drugs for the systemic management of moderate to severe pain. Control of the rate and duration of drug delivery is particularly important for systemic transdermal delivery of analgesic drugs to avoid the potential risk of overdose and the discomfort of an insufficient dosage.

One class of analgesics that has found application in a transdermal delivery route is the synthetic opiates, a group of 4-aniline piperidines. The synthetic opiates, e.g., fentanyl and certain of its derivatives such as sufentanil and alfentanyl, are particularly well-suited for transdermal administration. These synthetic opiates are characterized by their rapid onset of analgesia, high potency, and short duration of action. They are estimated to be 80 and 800 times, respectively, more potent than morphine. These drugs, in the form utilized, are weak bases, i.e., amines, whose major fraction is cationic in acidic solution. Further, these drugs or agents have polybasic anionic counter ions e.g, citrate, tartrate, and maleate.

The amine drugs preferably used in this invention are available pharmaceutically as citrates, e.g., fentanyl citrate, sufentanil citrate. In vitro and in vivo studies of iontophoretic delivery of these analgesic citrates have been reported. See, e.g., Thysman and Preat, Anesth. Analg., vol. 77 (1993) 61–66. In an in vivo study to determine plasma concentration, Thysman and Preat compared simple diffusion of fentanyl and sufentanil to iontophoretic delivery in citrate buffer at pH 5. Simple diffusion did not produce any detectable plasma concentration. The plasma levels attainable depended on the maximum flux of the drug that can cross the skin and the drug's pharmacokinetic clearance variables. Iontophoretic delivery was reported to have a significantly reduced lag time (i.e., time required to achieve peak plasma levels) as compared to passive transdermal patches (1.5 h versus 14 h). Thus, active electrotranstophoretic delivery of drugs over passive delivery of these drugs, many issues remain. For example, fentanyl, in acidic solution exists as the cation $FH^+$ where F represents fentanyl. Fentanyl citrate, a pharmaceutically available form of fentanyl having a polybasic citrate anion, appears to involve only one of the three carboxylic acid groups of citric acid in salt formation with the fentanyl. At the pH for optimized permselectivity of skin, namely, pH≅6.0, the remaining two carboxylic acid groups are ionized and the protons ($H^+$) generated in ionization compete with $FH^+$ for delivery in the electrotransport process. This competition reduces the overall efficiency of delivery of $FH^+$ agent.

Previous work has involved the neutralization of fentanyl citrate with bases such as sodium or potassium hydroxide. It has been found that such neutralizations of fentanyl citrate with sodium or potassium hydroxide, achieve little more than introducing another small monovalent cation which, similar to protons, competes with fentanyl cation for delivery during an electrotransport process.

To date, the art has not adequately responded with a solution to this problem of reducing competitive ions in the electrotransport process.

SUMMARY OF THE INVENTION

The present invention provides an improved electrotransport device and method for delivering a therapeutic agent through a body surface by electrotransport where the therapeutic agent comprises, in solution, an agent cation and a polybasic anionic counter ion. The electrotransport device comprises a donor reservoir containing a solution of the therapeutic agent to be delivered and a compound, the compound in solution forming a metal cation M and a pH-increasing anion X, the metal cation M having a valency of at least +2 and being reactive with said polybasic anionic counter ion to form a complex. The method comprises placing the solution in therapeutic agent-transmitting relation to a body surface and delivering the therapeutic agent through the body surface by electrotransport.

A further aspect of the present invention is a method for adjusting the pH of a solution of a therapeutic agent in a donor reservoir of an electrotransport delivery device. The method comprises placing, in the solution of the therapeutic agent, a multivalent metal compound of the formula:

wherein:

M is a metallic cation having a valency of at least +2 and being reactive with said polybasic anionic counter ion to form a complex, and X is a pH-increasing anion.

M is preferably selected from the group consisting of aluminum, calcium, cobalt, copper, iron, nickel, titanium and zinc. X is preferably selected from the group consisting of oxide, hydroxide, carbonate, alkoxide, alkyl, hydrides, acetonylacetonate and mixed acetonylacetonate-alkoxide. Most preferred are those compounds of formula I in which M is calcium, zinc or aluminum, and X is oxide or hydroxide. The therapeutic agent is preferably a salt, is more preferably an amine, and is most preferably is an amine salt selected from the group consisting of fentanyl citrate, sufentanil citrate and alfentanil citrate.

In another aspect, the present invention is an amine drug complex of the formula:

wherein $R_1$ and $R_2$ may be the same or different and are selected from the group consisting of —H, —OH, lower alkyl, carboxyl, or alkoxy; $R_3$ is selected from the group consisting of —H, —OH, lower alkyl or alkoxy; $R_4$ and $R_5$ may be the same or different and are selected from the group consisting of —H, —OH, alkyl, lower alkyl, alkoxy, or carboxyl; Y is the amine drug to be delivered; M is a metallic cation; and n is an integer having a value of two or greater. Preferably, the formation constant for the amine complex of formula (II) is $1\times10^4$.

In a preferred aspect, the invention is a complex of the formula:

wherein M is a metallic cation selected from the group consisting of aluminum, calcium, cobalt, copper, iron, nickel, titanium and zinc; Y is fentanyl, sufentanil or alfentanil; n is an integer of value 2 or greater and wherein the formation constant for the metal complex (III) is greater than about $1\times10^4$. The preferred complex of formula (III) has $R_1$, $R_2$, $R_4$, and $R_5$ of formula (II) comprising hydrogen (—H) and $R_3$ comprising hydroxyl (—OH).

In yet further aspect, the invention provides a drug reservoir for an iontophoresis device. The reservoir includes an agent to be delivered iontophoretically, a hydrogel disc saturated with the agent, having opposite sides, and a multivalent metal compound of formula (I) layered on one side of the hydrogel disc. The agent to be delivered is fentanyl, sufentanil or alfentanil, and is suitably in the form of a salt of a polycarboxylic acid. Alternatively, the hydrogel disc contains both the agent salt and the metal compound of formula (I). The hydrogel disc may comprise essentially any suitable hydrogel. Preferably, the disc comprises a hydrogel selected from the group consisting of synthetic polymers such as poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxyethyl methacrylate), poly(vinyl alcohol), and poly (allyl alcohol). Hydroxyl functional condensation polymers (i.e., polyesters, polycarbonates, polyurethanes) are also examples of suitable synthetic polymers. Naturally occurring polymers (or derivatives thereof suitable for use as the gel matrix are exemplified by cellulose ethers, methyl cellulose ethers, cellulose and hydroxylate cellulose, methyl cellulose and hydroxylated methyl cellulose, gums such as guar, locust, karaya, xanthan, gelatin and derivatives thereof.

In yet another aspect, the invention provides an iontophoretic device. The device includes a donor electrode including a drug reservoir; a counter electrode; and an electrical energy source electrically connected to the donor electrode and the counter electrode. The drug reservoir includes an agent to be delivered iontophoretically, a hydrogel disc saturated with the agent, having opposite sides, and a multivalent metal compound of formula (I) layered on one side of the hydrogel disc. The agent to be delivered is fentanyl, sufentanil or alfentanil, and is in the form of a salt of a polycarboxylic acid. Alternatively, the hydrogel disc contains both the agent salt and the metal compound of formula (I). The hydrogel disc comprises a hydrogel as was described above. The multivalent metal compound is also described above and preferably comprises a compound of formula (I).

As used herein, the term "treating" should be broadly construed to include, but not be limited to, "reacting," "precipitating," "complexing," "chelating" and "mixing."

As used herein the term "polybasic anionic counter ion" is intended to mean, with exemplary reference to carboxylic acids, any carboxylic acid having two or more hydrogen atoms available for salt formation. Di-, tri- and tetracarboxylic acids (and higher) are contemplated by this invention but should not be construed as limiting thereof. For example, and without limitation, this term contemplates within its scope, polyacrylic acid, polymethacrylic acid, and generally, any polycarboxylic acid. Another family of polybasic anionic counter ion would be the copolymers of styrene/maleic acid. One skilled in the art will be able to apply this definition to other chemical species.

As used herein and generally used in the art, the terms "polydentate" or "bidentate" refer to the number of coordinate bonds that a single ligand forms with a metal ion. Those terms are largely synonymous with the term "polybasic" as defined above.

Other advantages and a fuller appreciation of specific adaptations, compositional variations, and physical attributes of the present invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWINGS

The preferred exemplary embodiment of the present invention will hereinafter be described in conjunction with the appended drawing in which.

MODES FOR CARRYING OUT THE INVENTION

The present invention relates broadly to improved methods for the iontophoretic delivery of therapeutic agents and to a delivery system therefor. More specifically, the present invention is particularly well-adapted for the administration, by electrotransport delivery, of certain drugs or therapeutic agents. The preferred therapeutic agents in a practice of this invention are basic, are preferably amines, and most preferably as fentanyl and related species as was described above. Accordingly, the present invention will now be described in detail with respect to such preferred species. However, those skilled in the art will appreciate that such a description of the invention is meant to be exemplary only and should not be viewed as limitative of the full scope thereof.

In one of its aspects, the present invention is a method for increasing flux in iontophoretic drug delivery of an amine drug salt or amine therapeutic agent. Amine drug salts for treatment in accordance with a preferred practice of the present invention are selected from the synthetic opiates of the 4-aniline piperidine group. Like many therapeutic agents, these compounds exist as cations in aqueous solution. These synthetic opiates are pharmaceutically available as citrate salts. Preferred synthetic opiates in accordance with this invention are the amine citrate salts of e.g., fentanyl citrate, sufentanil citrate and alfentanil citrate.

An aqueous solution of fentanyl citrate (20 mg of free fentanyl base/ml) has a pH of about 3.8. It has been found that if amine salts are treated, i.e., neutralized, with a multivalent metal compound such as an oxide or a hydroxide, e.g., zinc oxide or calcium hydroxide, the pH is increased and the electrotransport of the drug cation is increased. Addition of a stoichiometric amount of the metal compound (i.e., addition of 1 mole of metal compound/mole of citrate anion) increases the pH to about 5 to 6, the optimal pH for permselectivity of skin.

In amine citrate salts such as fentanyl citrate, only one of the carboxylic acid groups of the citric acid is involved in salt formation with the opiate amine. The two remaining carboxylic acid groups are ionized and the protons compete with the fentanyl cation, $FH^+$, for electrotransport. However, polycarboxylic acids, such as citric acid, act also as polydentate ligands, i.e., the carboxylic acid groups act as ligands. Generally, multivalent metal ions bond strongly to polydentate ligands. Therefore, without intending to be bound by theory, a proposed mechanism for the results achieved by the method of the present invention is that reaction of the carboxylic acid groups with multivalent metal bases results in complexation between the metal ion and the carboxylate groups, i.e., the acid groups act as a bidentate ligand to complex the metal ion. Such neutralization/complexation is given by the following equation which illustrates fentanyl citrate as the salt and zinc oxide as the multivalent metal base compound:

-continued

In such a reaction, the concentration of the multivalent metal ion in aqueous solution is greatly diminished compared to noncomplexing metal ions such as sodium or potassium wherein sodium or potassium hydroxides are used to neutralize the acid groups. If the metal ion concentration in solution is negligible, then the electrotransport of the fentanyl cation will not be decreased.

The stability of metal complexes with ligands is described by the formation constant, $K_1$ which provides a measure of the equilibrium between the complexed and uncomplexed metal ions as illustrated below.

$$M^{n+} + L^{3-} \rightleftharpoons ML^{+n-3}$$

where $M^{n+}$ is the metal cation, as described hereinabove, and L is a ligand with −3 charge such as citrate. The formation constant K is, therefore, $$K = \frac{[ML^{+n-3}]}{[M^{n+}][L^{-3}]}$$

If K for the complexing of the metal ion with a ligand is large, then the concentration of the metal ion in solution is small. In this instance, the metal ions in accordance with the present invention are strongly bound to the two carboxylate groups of, e.g., fentanyl citrate. Therefore, the concentration of free metal ion resulting from complexation with the amine salt drug is typically <0.05 mM (or less than about 0.01% of the therapeutic agent) and the formation constant K is in the range of about $1 \times 10^{+4}$ to about $1 \times 10^{-8}$ or greater.

In another aspect, the present invention is a composition of an amine drug that provides enhanced iontophoretic delivery of the amine drug, in an aqueous medium, to a subject. The composition comprises, in aqueous medium, the complex of formula:

(III)

wherein YH$^+$ is a cation drug selected from the group consisting of fentanyl, sufentanil and alfentanil; M is a multivalent metal ion selected from the group consisting of aluminum, calcium, cobalt, copper, iron, nickel, titanium and zinc; n is an integer of value 2 or greater and wherein the formation constant for the M—COO$^-$ bond is greater than $1 \times 10^4$. Preferred are those compositions of formula (III) wherein M is zinc, calcium and aluminum, and the pH of the complex of formula (III) in aqueous medium is about 5 to 6.

Complex formation and improved electrotransport was first confirmed by model compound studies in which N-methylpiperidine, a compound structurally similar to fentanyl, was reacted with the compounds of formula (I). The infrared (IR) spectrum of N-methylpiperidine citrate was compared with the IR spectrum of a complex formed by addition of a stoichiometric amount of zinc oxide to an aqueous solution of N-methylpiperidine citrate. The IR spectrum was consistent with the derived compound and distinctly different from that of zinc citrate and N-methylpiperidine citrate.

Improved electrotransport for opiate amine citrates has been demonstrated in accordance with the present invention. Fentanyl citrate, neutralized with compounds of formula (I), was provided in an electrotransport device and the electrotransport flux measured. It has been found that treatment with the metal compound of formula (I) improves the electrotransport flux ($\mu g/cm^2$-hr) of fentanyl by between about 25% to about 150%.

It will be appreciated by those working in the field that the present method can be used in conjunction with a wide variety of electrotransport drug delivery systems, as the method is not limited in any way in this regard. For examples of electrotransport drug delivery systems, reference may be had to U.S. Pat. Nos. 5,147,296 to Theeuwes et al., 5,080,646 to Theeuwes et al., 5,169,382 to Theeuwes et al., and 5,169,383 to Gyory et al., the disclosures of which are incorporated by reference herein.

Figure 1:
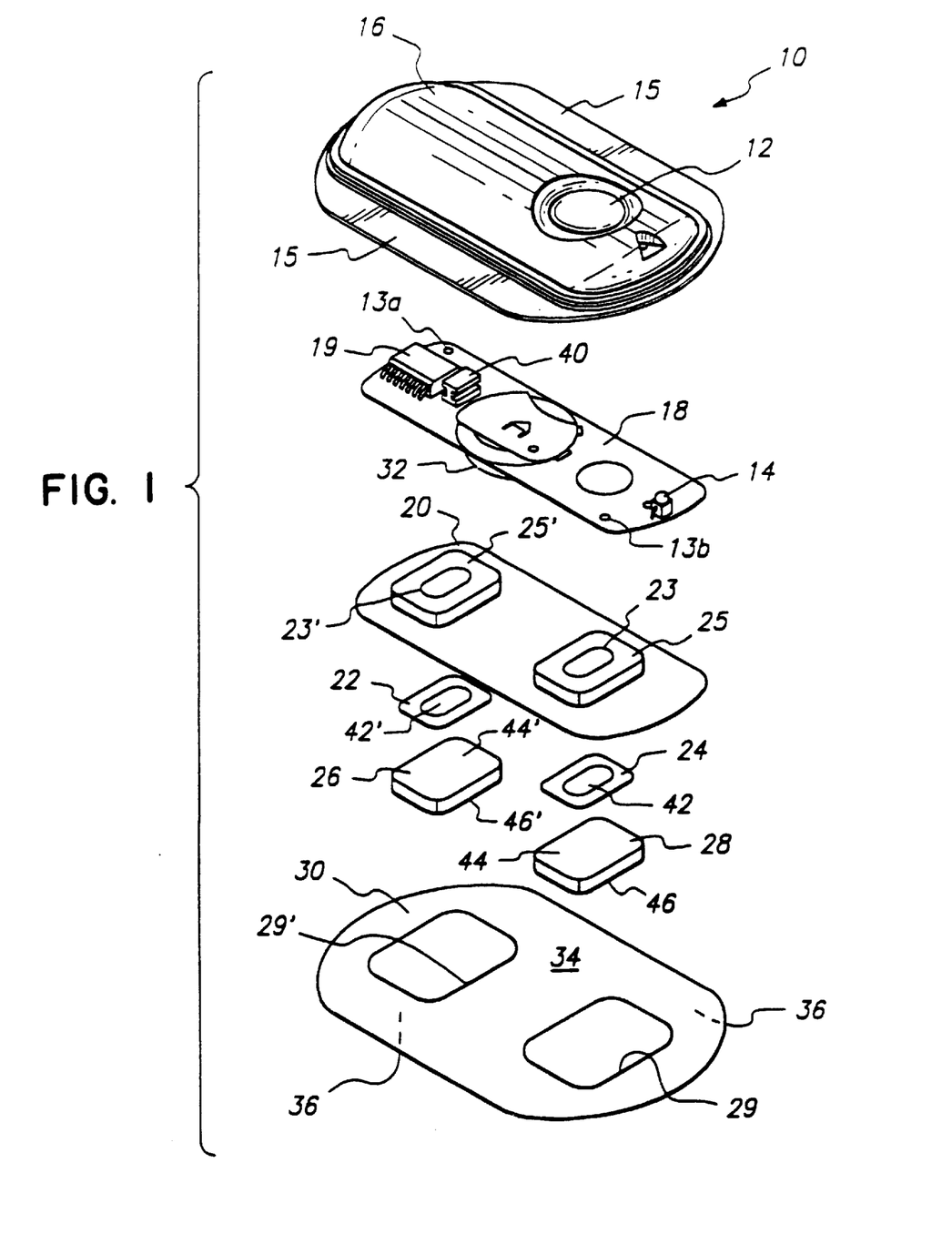
FIG. 1 is an exploded view of an electrotransport drug delivery device in accordance with the present invention.

FIG. 1 illustrates a representative electrotransport delivery device that may be used in conjunction with the present method. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate). Printed circuit board assembly 18 comprises an integrated circuit 19 coupled to discrete components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a button cell battery 32. Other types of batteries may also be employed to power device 10.

The device 10 is generally comprised of battery 32, electronic circuitry 19, 40, electrodes 22, 24, and drug/chemical reservoirs 26, 28, all of which are integrated into a self-contained unit. The outputs (not shown in FIG. 1) of the circuit board assembly 18 make electrical contact with the electrodes 24 and 22 through openings 23, 23' in the depressions 25, 25' formed in lower housing 20, by means of electrically conductive adhesive strips 42, 42'. Electrodes 22 and 24, in turn, are in direct mechanical and electrical contact with the top sides 44', 44 of drug reservoirs 26 and 28. The botton sides 46', 46 of drug reservoirs 26, 28 contact the patient's skin through the openings 29', 29 in adhesive 30.

Device 10 optionally has a feature which allows the patient to self-administer a dose of drug by electrotransport. Upon depression of push button switch 12, the electronic circuitry on circuit board assembly 18 delivers a predetermined DC current to the electrodes/reservoirs 22, 26 and 24, 28 for a delivery interval of predetermined length. The push button switch 12 is conveniently located on the top side of device 10 and is easily actuated through clothing. A double press of the push button switch 12 within a short time period, e.g., three seconds, is preferably used to activate the device for delivery of drug, thereby minimizing the likelihood of inadvertent actuation of the device 10. Preferably, the device transmits to the user a visual and/or audible confirmation of the onset of the drug delivery interval by means of LED 14 becoming lit and/or an audible sound signal from, e.g., a "beeper". Drug is delivered through the patient's skin by electrotransport, e.g., on the arm, over the predetermined delivery interval.

Anodic donor electrode 22 is preferably comprised of silver and cathodic counter electrode 24 is preferably comprised of silver chloride. Both reservoirs 26 and 28 are preferably comprised of polymer hydrogel materials. Electrodes 22, 24 and reservoirs 26, 28 are retained by lower housing 20.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (e.g., polyethylene) which can be easily molded to form depressions 25, 25' and cut to form openings 23, 23'. The assembled device 10 is preferably water resistant (i.e., splash proof) and is most preferably waterproof. The system has a low profile that easily conforms to the body, thereby allowing freedom of movement at, and around, the wearing site. The reservoirs 26 and 28 are located on the skin-contacting side of the device 10 and are sufficiently separated to prevent accidental electrical shorting during normal handling and use.

The device 10 adheres to the patient's body surface (e.g., skin) by means of peripheral adhesive 30 which has upper side 34 and body-contacting side 36. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and drug reservoirs within housing depressions 25, 25' as well as retains lower housing 20 attached to upper housing 16.

The reservoirs 26 and 28 generally comprise a gel matrix, with the drug solution uniformly dispersed in anodic reservoir 26. Drug concentrations in the range of approximately $1 \times 10^{-4}$ M to 1.0 M or more can be used, with drug concentrations in the lower portion of the range being preferred. Suitable polymers for the gel matrix may comprise essentially any synthetic and/or naturally occurring polymeric materials. A polar nature is preferred when the active agent is polar and/or capable of ionization, so as to enhance agent solubility. Optionally, the gel matrix is water swellable. Examples of suitable synthetic polymers include, but are not limited to, poly(acrylamide), poly(2-hydroxyethyl acrylate), poly (2-hydroxypropyl acrylate), poly(N-vinyl-2-pyrrolidone), poly(n-methylol acrylamide), poly(diacetone acrylamide), poly(2-hydroxylethyl methacrylate), poly(vinyl alcohol) and poly(allyl alcohol). Hydroxyl functional condensation polymers (i.e., polyesters, polycarbonates, polyurethanes) are also examples of suitable polar synthetic polymers. Polar naturally occurring polymers (or derivatives thereof) suitable for use as the gel matrix are exemplified by cellulose ethers, methyl cellulose ethers, cellulose and hydroxylated cellulose, methyl cellulose and hydroxylated methyl cellulose, gums such as guar, locust, karaya, xanthan, gelatin, and derivatives thereof. Ionic polymers can also be used for the matrix provided that the available counterions are either drug ions or other ions that are oppositely charged relative to the active agent.

The adjusted pH drug solution of the present invention is incorporated into the drug reservoir, e.g., a gel matrix as just described, and administered to a patient using an electrotransport drug delivery system, optionally as exemplified hereinabove. Incorporation of the drug solution can be done any number of ways, i.e., by imbibing the solution into the reservoir matrix, by admixing the drug solution with the matrix material prior to hydrogel formation, or by imbibing the solution into the reservoir matrix after formation of the matrix. Alternatively, the drug and compound MX can be placed in a dry donor reservoir matrix and a liquid solvent (e.g., water) is later added to the dry matrix (e.g., at the time of use).

The compound MX is preferably dispersed throughout the donor reservoir 26. Most preferably, the molar loading of compound MX is about equal to the molar loading of the therapeutic agent in reservoir 26. By virtue of the way in which the pH of the formulation is adusted, introduction of competitive ions or extraneous contaminants is avoided and drug flux is optimized.

The donor reservoir 26 typically has a skin-contact area in the range of about 1 $cm^2$ to about 50 $cm^2$. Generally speaking, a current in the range of about 50 to 5000 $\mu A$ is employed during drug delivery.

As was noted above, the present invention is applicable to the electrotransport delivery of essentially any therapeutic species comprising an agent cation and a polybasic anionic counter ion. Examples of other therapeutic species to which this invention is likely to include, without limitation, lisuride maleate, loxapine succinate, metaraminol bitartrate and oxalate dihydrate, epinephrine bitartrate, brovincamine fumarate, diethylcarbamazine citrate, dimethidene maleate, dextromoramide tartrate, acepromazine citrate, diethylcarbamazine citrate. Generally speaking, zinc oxide will be the preferred species MX with which to react the selected therapeutic agent. One skilled in the art understanding the full scope of this invention will likely recognize that there are many further therapeutic species to which this invention may apply.

The present invention is further explained by the following examples which should not be construed by way of limiting the scope of the present invention. Process steps described in the examples are carried out at room temperature and atmospheric pressure unless otherwise specified.

EXAMPLE 1

Demonstration of Neutralization and Complex Formation with Calcium Hydroxide

A model compound study was initiated to investigate the reaction between an amine citrate salt and calcium hydroxide, i.e., specifically to evaluate the ability of calcium hydroxide to adjust the pH of citrate salt solutions. The amine chosen was N-methylpiperdine because of its structural similarity to the synthetic opiate agents.

N-methylpiperidinium citrate was prepared by the reaction of citric acid and N-methylpiperidine in ethanol. Citric acid and ethanol were mixed at 25° C. until completely dissolved. N-methylpiperidine was added dropwise to the citric acid solution over 5 minutes. The salt was recrystallized from hot ethanol and the IR spectrum was run and found to be consistent with the desired compound.

Into 10 ml of an aqueous solution 0.05 mM N-methylpiperidinium citrate were added (an equimolar amount) 0.37 g of calcium hydroxide. After stirring the solution at 25° C. for about 5 minutes, a clear solution formed. A white precipitate formed after approximately 30 minutes. The IR spectrum of the isolated precipitate matched the spectrum of calcium citrate. The intermediate where a calcium ion was bound to two acid groups of the citrate molecule was not isolated. The addition of calcium hydroxide adjusted the pH of the solution from 3.7 to 6.1. The results show that calcium hydroxide is useful for adjusting the pH of citrate drug salts.

EXAMPLE 2

Demonstration of Neutralization and Complex Formation with Zinc Oxide

A similar study was initiated as in Example 1 to evaluate the ability of ZnO to adjust the pH of an aqueous solution of N-methylpiperidinium citrate. The addition of zinc oxide yielded slightly different results in that the reaction did not produce zinc citrate as a precipitate.

N-methylpiperidinium citrate was prepared as described in Example 1. Into a 10 ml of an aqueous solution of 0.05 mM N-methylpiperidinium citrate was added an equimolar amount (0.005 mol) of zinc oxide. A zinc complex was isolated by precipitation with isopropyl alcohol and recrystallized from hot isopropyl alcohol/water. The IR spectrum of the resulting complex was consistent with the desired product, i.e., the zinc ion bound to the two acid groups, and distinctly different from the IR spectrum of zinc citrate. The addition of zinc oxide adjusted the pH of the solution from 3.7 to 5.7. The results show that zinc oxide is useful for adjusting the pH of citrate drug salts.

EXAMPLE 3

Neutralization and Complex Formation using a Hydrogel Reservoir coated with Calcium Hydroxide In this experiment, the pH of hydrogels (suitable as a donor reservoir) containing N-methylpiperidinium citrate was adjusted with the addition of calcium hydroxide. Hydrogel discs suitable for use in an electrotransport device having the following formulation were prepared by techniques known in the art as follows.

| Material | % by Weight |
| --- | --- |
| Deionized Water | 83.5 |
| Non-ionic Guar | 0.5 |
| Glycerol | 5.0 |
| Mowiol 66-100 | 10.0 |
| Methocel K100 MP | 1.0 |

N-methylpiperidinium citrate was weighed on a piece of weighing paper and transferred to the surface of the hydrogel disc. The amine citrate salt, being very water soluble, diffused into the hydrogel disc in less than five minutes. These imbibed gel discs were stored in sealed pouches at 5° C. The gel pH was measured after 24 hours. Calcium hydroxide was spread evenly on one side of the hydrogel discs with a spatula. The pH of these hydrogels was measured at 72 and 168 hours after the application of calcium hydroxide. The results are shown in Table 1.

TABLE 1

| Gel # | mol NMP-CT* | pH @ 24 hrs. | mg Ca(OH)$_2$ | mol Ca(OH)$_2$ | pH @ 72 hrs. | pH @ 168 hrs. |
| --- | --- | --- | --- | --- | --- | --- |
| 1 | 1.18 × 10$^{-4}$ | 4.0 | 9.06 | 1.22 × 10$^{-4}$ | 5.7 | 5.8 |
| 2 | 1.18 × 10$^{-4}$ | 4.1 | 6.73 | 0.91 × 10$^{-4}$ | 5.0 | 5.2 |
| 3 | 1.20 × 10$^{-4}$ | 4.1 | 4.54 | 0.61 × 10$^{-4}$ | 4.6 | 4.7 |

*NMP-CT = N-methylpiperidinium citrate

The reaction in the hydrogels correlated with the reactions observed in the solution of Example 1. As seen from Table 1, the addition of calcium hydroxide neutralized the pH of the hydrogels. Table 1 also illustrates that as the molar ratio of metal compound to citrate salt approaches 1:1, enhanced neutralization occurs. After 7 days a white solid was observed on the surface of the discs. The solid was a mixture of unreacted calcium hydroxide and/or calcium citrate.

EXAMPLE 4

Neutralization and Complex Formation using a Hydrogel Reservoir coated with Zinc Oxide Hydrogel discs prepared as described in Example 3 were imbibed with N-methylpiperidinium citrate. The gel pH was measured after storing the gel in a sealed pouch at 5° C. for 24 hours. Zinc oxide was then spread evenly on one side of the hydrogel discs with a spatula. The gels were stored in a sealed pouch for another 24 hours, and the pH was measured. After six and seven days (i.e., 144 hrs. and 168 hrs. after application), the pH of the gels was remeasured. The results are shown in Table 2. No unreacted zinc oxide was observed on the surface of the gels.

TABLE 2

| Gel # | mol NMP-CT | pH @ 24 hrs. | mol ZnO added | pH @ 24 hrs. | pH @ 144 hrs. | pH @ 168 hrs. |
| --- | --- | --- | --- | --- | --- | --- |
| 1 | 1.17 × 10$^{-4}$ | 3.8 | 1.20 × 10$^{-4}$ | 6.6 | 5.6 | 5.3 |
| 2 | 1.18 × 10$^{-4}$ | 3.8 | 0.91 × 10$^{-4}$ | 4.4 | 4.6 | 4.4 |
| 3 | 1.19 × 10$^{-4}$ | 3.8 | 0.61 × 10$^{-4}$ | 4.5 | 4.4 | 4.3 |

The reaction in the hydrogels correlated with the reactions observed in the solution of Example 2. Zinc oxide reacted with N-methylpiperidinium citrate and effectively neutralized the hydrogels. Table 2 also illustrates that as the molar ratio of metal compound to citrate salt approaches 1:1, enhanced neutralization occurs. The relatively large pH shift observed in the gel resulted from some of the zinc oxide remaining unreacted with the N-methylpiperidinium citrate in the gel. As more zinc oxide reacted, the pH decreased.

EXAMPLE 5

Neutralization and Complex Formation using a Fentanyl imbibed Hydrogel

Hydrogel discs containing either zinc oxide or calcium hydroxide were prepared from mixtures having the following formulation:

| Material | % by Weight |
| --- | --- |
| Non-ionic Guar | 0.5 |
| Glycerol | 5.0 |
| Mowiol 66-100 | 8.0 |
| Methocel K100 MP | 1.0 |
| Cholestyramine | 10.0 |
| Zinc Oxide | 0.31 |
| or | |
| Calcium Hydroxide | 0.28 |
| Deionized Water | balance |

These hydrogels were imbibed with fentanyl citrate in a 1:1 molar ratio with the metal compound in the gel. Hydrogels of this formulation without the metal agents exhibit a pH of 3.8. The addition of calcium hydroxide or zinc oxide into the hydrogels raised the pH to 5.8.

The hydrogels of this example were then incorporated into electrotransport devices to assess fentanyl delivery across human epidermis samples. These systems applied a current of 100 $\mu$A through a drug releasing area of 1 cm$^2$ and the electrotransport flux measuring the results are shown in Table 3.

TABLE 3

Steady State Summary

| Added Metal Compound | Avg. Flux ($\mu$g/cm$^2$-hr.) | Std. Dev. |
| --- | --- | --- |
| None | 11.8 | 2.4 |
| Zinc Oxide | 15.2 | 2.1 |
| Calcium Hydroxide | 29.7 | 4.2 |

Table 3 shows that at steady state, both zinc oxide and calcium hydroxide enhance the flux of fentanyl through the skin. However, addition of calcium hydroxide greatly enhanced the fentanyl flux of the system compared to a device run under the same conditions without complex formation.

EXAMPLE 6

Epinephrine bitartrate is dissolved in water to create an aqueous solution. The epinephrin bitartrate solution is further mixed with zinc oxide. Addition of zinc oxide to the epinephrin bitartrate solution raises its pH and creates a complex. The complex exhibits enhanced delivery by electrotransport.

In summary, the present invention provides a method for improving the electrotransport of basic, primarily amine drug salts, primarily salts of the synthetic opiates, by treating, prior to iontophoretic delivery, i.e., neutralizing and complexing, the acid groups not involved in salt formation. The invention also provides an amine metal citrate complex form of the synthetic opiates that facilitates the electromigration of these drugs in their cation form. An iontophoretic device using the method of the invention is also provided.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

I claim:

1. A method of delivering a therapeutic agent through a body surface using electrotransport wherein the therapeutic agent comprises an agent cation and a polybasic counter ion, the method comprising the steps of:
   providing a solution of the therapeutic agent and a compound, the compound comprising a metal cation, M and a pH-increasing anion X, M having a valency of at least +2 and being capable of complexing with said polybasic anion;
   placing the solution in therapeutic agent-transmitting relation to a body surface; and
   delivering the therapeutic agent through the body surface using electrotransport.

2. The method of claim 1, wherein the compound has the formula:

MX wherein:
   M is selected from the group consisting of aluminum, calcium, cobalt, copper, iron, nickel, titanium and zinc; and
   X is selected from the group consisting of oxide, hydroxide, carbonate, alkoxide, alkyl, hydrides, acetonylacetonate and mixed acetonylacetonate-alkoxide.

3. The method of claim 1, wherein M is selected from the group consisting of calcium, zinc and aluminum, and X is selected from the group consisting of hydroxide and oxide.

4. The method of claim 1, wherein adding compound MX to the solution raises solution pH at least 2 pH units.

5. The method of claim 4, wherein adding compound MX to the solution raises solution pH to a level at which permselectivity of the body surface to electrotransport flux of the therapeutic agent is enhanced.

6. The method of claim 1, wherein the body surface is skin and the solution has a pH in the range of about 5 to about 7.

7. The method of claim 1, wherein said polybasic anionic counter ion is selected from the group consisting of citrate, oxalate, malonate, succinate, glutarate, adipate, pimelate, maleate, polyacrylate, polymethacrylate, polyacrylamidomethanesulfonate, fumarate, and mixtures thereof.

8. The method of claim 1, wherein said polybasic anionic counter ion is citrate.

9. The method of claim 1, wherein the compound is added to the solution in an amount which substantially minimizes the concentration of non-complexed M in solution.

10. The method of claim 1, wherein said therapeutic agent is a citrate drug salt.

11. The method of claim 1, wherein complexation of the metal cation M with the polybasic anionic counter ion has a complex formation constant which is greater than about $1 \times 10^4$.

12. The method of claim 1, wherein the solution comprises an aqueous solution.

13. A donor reservoir for an electrotransport device which delivers a therapeutic agent through a body surface, the donor reservoir containing a solution comprising:
   a therapeutic agent to be delivered wherein the agent comprises an agent cation and a polybasic anionic counter ion; and
   a compound wherein the compound comprises a metal cation M having a valency of at least +2 and a pH-increasing anion X, the cation M being capable of complexing with the polybasic anionic counter-ion.

14. The donor reservoir of claim 13, wherein the compound has the formula:

MX wherein:
   M is selected from the group consisting of aluminum, calcium, cobalt, copper, iron, nickel, titanium and zinc; and
   X is selected from the group consisting of oxide, hydroxide, carbonate, alkoxide, alkyl, hydrides, acetonylacetonate and mixed acetonylacetonate-alkoxide.

15. The donor reservoir of claim 14, wherein MX is zinc oxide.

16. The donor reservoir of claim 13, wherein the compound is added to the reservoir in order to raise its pH.

17. The donor reservoir of claim 16, wherein the reservoir pH is in the range where the permselectivity of the body surface to electrotransport flux of the therapeutic agent is enhanced.

18. The donor reservoir of claim 16, wherein the body surface is skin and the reservoir pH is in the range of about 5 to about 7.

19. The donor reservoir of claim 16, wherein said polybasic anionic counter ion is selected from the group consisting of citrate, oxalate, malonate, succinate, glutarate, adipate, pimelate, maleate, polyacrylate, polymethacrylate, polyacrylamidomethanesulfonate, fumarate, and mixtures thereof.

20. The donor reservoir of claim 13, wherein said polybasic anionic counter ion is citrate.

21. The donor reservoir of claim 13, wherein a stoichiometric amount of said compound is added to the donor solution.

22. The donor reservoir of claim 13, wherein said therapeutic agent is a citrate drug salt.

23. The donor reservoir of claim 13, wherein the complexation of the metal cation M with the polybasic anionic counter ion has a complex formation constant which is greater than $1 \times 10^4$.

24. The donor reservoir of claim 13, wherein the reservoir comprises an aqueous solution of the therapeutic agent.

25. The donor reservoir of claim 13, wherein the reservoir comprises a matrix which contains a solution of the therapeutic agent.

26. The donor reservoir of claim 25, wherein the matrix comprises a hydrophilic polymer.

27. An electrotransport therapeutic agent delivery device comprising the donor reservoir of claim 13.

28. An amine drug complex of the formula:

wherein $R_1$ and $R_2$ may be the same or different and are selected from the group consisting of H, —OH, lower alkyl, carboxyl, or alkoxy;

$R_3$ is selected from the group consisting of —H, —OH, lower alkyl or alkoxy;

$R_4$ and $R_5$ may be the same or different and are selected from the group consisting of —H, —OH, alkyl, lower alkyl, alkoxy, or carboxyl and wherein Y is selected from the group consisting of fentanyl, sufentanil, or alfentanyl, M is a metallic cation, and n is an integer having a value of two or greater.

29. An amine drug complex according to claim 28 wherein the formation constant for the metal complex is greater than $1 \times 10^4$.

30. A composition of an amine drug complex of formula:

wherein M is a metallic cation selected from the group consisting of aluminum, calcium, cobalt, copper, iron, nickel, titanium and zinc, Y is fentanyl, sufentanil or alfentanil; and wherein the formation constant for the metal complex is greater than $1 \times 10^4$.

* * * * *

UNITED STATES PATENT AND TRADEMARK OFFICE
CERTIFICATE OF CORRECTION

PATENT NO. : 6,004,577
DATED : December 21, 1999
INVENTOR(S) : Thomas O. Murdock It is certified that error appears in the above-identified patent and that said Letters Patent is hereby corrected as shown below:

Title page,
Item [73], Assignee, should be added as follows:
-- Assignee: Alza Corporation, Palo Alto, CA (US) --

Signed and Sealed this

Twenty-eighth Day of June, 2005

JON W. DUDAS
*Director of the United States Patent and Trademark Office*